United States Patent
Xi et al.

(10) Patent No.: US 11,950,997 B2
(45) Date of Patent: Apr. 9, 2024

(54) ARTIFICIAL CORNEA WITH DOUBLE-SIDE MICROTEXTURED PHEMA HYDROGEL

(71) Applicant: THE TRUSTEES OF THE STEVENS INSTITUTE OF TECHNOLOGY, Hoboken, NJ (US)

(72) Inventors: Yiwen Xi, Hoboken, NJ (US); Chang-Hwan Choi, Tenafly, NJ (US); Xiaojun Yu, Fishers, IN (US); Junfeng Liang, Westfield, NJ (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 261 days.

(21) Appl. No.: 16/879,641

(22) Filed: May 20, 2020

(65) Prior Publication Data
US 2020/0390539 A1 Dec. 17, 2020

Related U.S. Application Data

(60) Provisional application No. 63/000,422, filed on Mar. 26, 2020, provisional application No. 62/850,430, filed on May 20, 2019.

(51) Int. Cl.
*A61F 2/14* (2006.01)
*A61L 27/02* (2006.01)
(Continued)

(52) U.S. Cl.
CPC ............ *A61F 2/145* (2013.01); *A61L 27/025* (2013.01); *A61L 27/48* (2013.01); *A61L 27/52* (2013.01);
(Continued)

(58) Field of Classification Search
CPC .......... A61F 2/145–2/1453; A61F 2002/0081; A61F 2210/0061; A61F 2220/0008;
(Continued)

(56) References Cited

U.S. PATENT DOCUMENTS 4,624,669 A * 11/1986 Grendahl ................. A61F 2/15
  128/899
4,985,559 A *  1/1991 Goldberg ............. C07D 513/04
  544/38
(Continued)

FOREIGN PATENT DOCUMENTS

WO   WO-2009135068 A1 * 11/2009 ............... A61F 2/14
WO       2013066615 A1    5/2013
WO      20170156460 A1    9/2017

OTHER PUBLICATIONS

Chirila, Traian V., "An overview of the development of artificial corneas with porous skirts and the use of PHEMA for such an application", Biomaterials 22, (2001), pp. 3311-3317.

(Continued)

*Primary Examiner* — Paul B Prebilic
(74) *Attorney, Agent, or Firm* — Clark Hill PLC; Ralph W. Selitto; John K. Kim

(57) ABSTRACT

An artificial cornea and an associated manufacturing method are disclosed. The artificial cornea has two sides, each of which has an associated microstructure. In an embodiment, microlines can be provided on an anterior side, and a posterior side can have micropores. Both the geometry of the microstructures and their dimensions can be customized for an individual patient. The geometry of the artificial cornea itself and its dimensions can also be customized as such. In addition, the lifetime of the artificial cornea can be significantly enhanced by adding co-polymer(s) into the hydrogel to strengthen its mechanical properties. Patient recovery can be aided by adding peptides into the artificial cornea surfaces to improve cell growth post-operation.

14 Claims, 8 Drawing Sheets

(51) Int. Cl.
 *A61L 27/48* (2006.01)
 *A61L 27/52* (2006.01)
 *A61F 2/00* (2006.01)

(52) U.S. Cl.
 CPC ... *A61F 2002/0081* (2013.01); *A61L 2430/16* (2013.01)

(58) Field of Classification Search
 CPC ..... A61F 2250/0023; A61F 2250/0026; A61L 27/025; A61L 27/48; A61L 27/52; A61L 2430/16
 See application file for complete search history.

(56) References Cited

U.S. PATENT DOCUMENTS

| | | | | |
|---|---|---|---|---|
| 5,292,514 | A * | 3/1994 | Capecchi | A61L 27/34 424/428 |
| 6,391,055 | B1 | 5/2002 | Ikada et al. | |
| 7,491,350 | B2 * | 2/2009 | Silvestrini | G02C 7/165 264/81 |
| 7,909,867 | B2 | 3/2011 | Myung et al. | |
| 2002/0095211 | A1 * | 7/2002 | Young | A61F 2/16 623/6.16 |
| 2005/0080485 | A1 * | 4/2005 | Nigam | A61F 2/147 623/5.11 |
| 2005/0177231 | A1 * | 8/2005 | Ricci | A61F 2/1613 623/6.16 |
| 2009/0248150 | A1 * | 10/2009 | Lehman | A61L 27/16 623/6.6 |
| 2012/0071580 | A1 * | 3/2012 | Cho | A61L 27/52 523/105 |
| 2012/0143325 | A1 * | 6/2012 | Christie | A61F 2/15 623/5.13 |
| 2014/0052245 | A1 * | 2/2014 | Zickler | A61F 2/1613 623/6.17 |
| 2015/0342725 | A1 * | 12/2015 | Cuevas | A61F 2/161 623/6.16 |
| 2018/0193133 | A1 * | 7/2018 | De Juan, Jr. | A61F 2/142 |
| 2020/0337834 | A1 * | 10/2020 | Webb | B29C 39/10 |

OTHER PUBLICATIONS

Parke-Houben, Rachel et al., "Interpreting polymer network hydrogel scaffolds for artificial cornea periphery", J. Mater Sci: Mater Med, vol. 26, Issue 107, Feb. 11, 2015, 12 pages.

Rosales-Leal, J.I. et al., "Effect of roughness, wettability and morphology of engineered titanium surfaces on osteoblast-like cell adhesion", Colloids and Surfaces A: Physicochemical and Engineering Aspects, vol. 365, (2010), pp. 222-229.

Zellander et al., "Characterization of Pore Structure in Biologically Functional Poly(2-Hydroxyethyl Methacrylate)—Poly (Ethylene Glycol) Diacrylate (PHEMA-PEGDA)", PLOS ONE, vol. 9, Issue 5, May 2014, 8 pages.

International Search Report and Written Opinion for PCT/US2021/024521, dated Jun. 28, 2021, 16 pages.

* cited by examiner

FIG. 1A
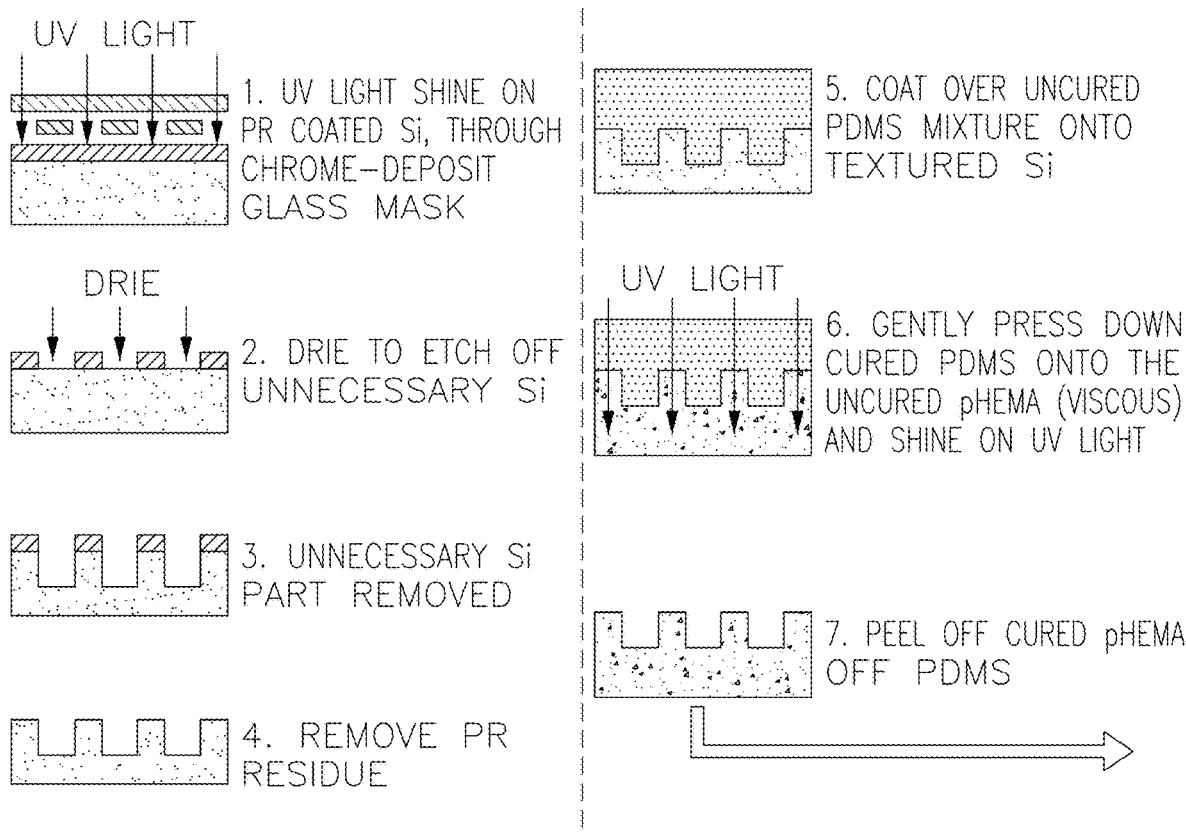
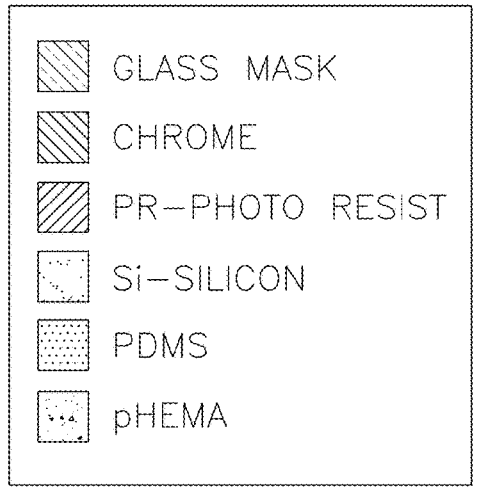

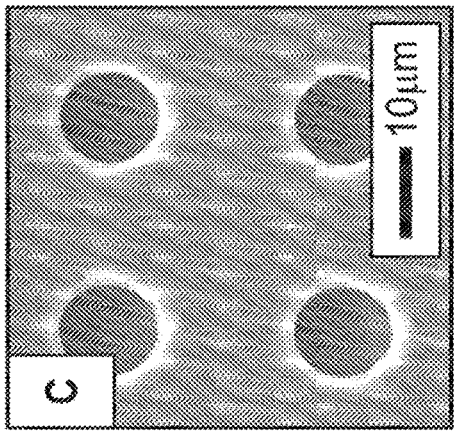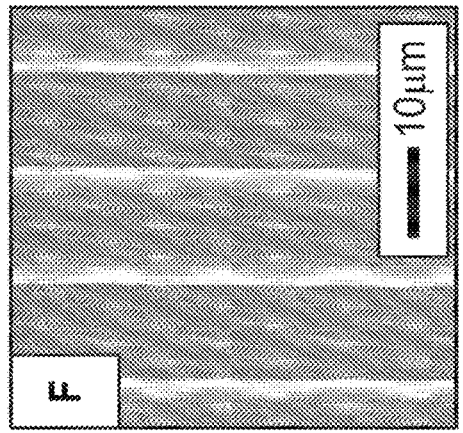

ARTIFICIAL CORNEA WITH DOUBLE-SIDE MICROTEXTURED PHEMA HYDROGEL

CROSS-REFERENCE TO RELATED APPLICATIONS

This Application claims the benefit of U.S. Provisional Application No. 62/850,430 filed May 20, 2019 and U.S. Provisional Application No. 63/000,422 filed Mar. 26, 2020. The entire disclosures of each of the aforesaid applications are incorporated herein by reference.

FIELD OF THE INVENTION

The present invention pertains to the production and use of a novel artificial cornea material. Specifically, it pertains to a biomaterial that integrates effectively with the native ocular cells.

BACKGROUND OF THE INVENTION

As stated by World Health Organization (WHO), over 10 million people suffer from corneal blindness globally and 285 million people are visually impaired; however, only 1/50 of the patients obtained corneal transplants each year worldwide due to lack of donor tissue. In addition, functional defects and heterogeneity of the transplanted cornea commonly occur within a few years of the surgery because of the prevalent use of tissue from older cornea donors. Rejection of donated tissue constitutes another substantive problem in the art.

Overall, full corneal translation from a donor is inefficient and inaccessible for many. A rising geriatric population and the increasing incidence of eye diseases worldwide are expected to be the prime factors driving the demand worldwide for keratoprosthesis (i.e., artificial cornea) treatment.

SUMMARY OF THE INVENTION

The present invention relates to an artificial cornea made of Poly(2-hydroxyethyl methacrylate) (pHEMA) hydrogel. The pHEMA is microtextured on both sides to facilitate integration of the artificial cornea with the native tissue of a patient. Specifically, the artificial cornea is designed so that it is biocompatible, driving rapid proliferation of corneal epithelial cells while also enhancing the adhesion of corneal fibroblasts. By fostering its integration with the epithelium as such, the artificial cornea limits the chances of infection, inflammation or extrusion. By integrating with the stroma, the stability of the material within the eye improves. These factors ultimately expedite recovery from surgical implantation. In addition, no donor tissue is required, and the risk of rejection is low. The current artificial cornea products on the market use the stiff materials like Poly(methyl methacrylate) (PMMA), of which Young's Modulus ranges from 2 to 3 GPa. Stiff materials are likely to increase the risks of tissue extrusion and inflammation. The pHEMA hydrogel is soft but durable with the Young's Modulus ranging from 1 to 10 MPa, making it ideal for permanent wearing while decreasing discomfort.

BRIEF DESCRIPTION OF THE FIGURES

The patent or application file contains at least one drawing executed in color. Copies of this patent or patent application publication with color drawing(s) will be provided by the Office upon request and payment of the necessary fee.

For a more complete understanding of the invention disclosed herein, reference is made to the following detailed description of an exemplary embodiment considered in conjunction with the accompanying drawings, in which:

FIG. 1A is a flow diagram of the production process of the microtextured pHEMA, with an associated legend;

FIG. 4A displays a pore size of 3 µm on the pHEMA hydrogel's microstructure patterned on silicon substrate as a scanning electron microscope image;

FIG. 4B displays a pore size of 6 µm on the pHEMA hydrogel's microstructure patterned on silicon substrate as a scanning electron microscope image;

FIG. 4C displays a pore size of 12 µm on the pHEMA hydrogel's microstructure patterned on silicon substrate as a scanning electron microscope image;

FIG. 4D displays a line gap size of 3 µm on the pHEMA hydrogel's microstructure patterned on silicon substrate as a scanning electron microscope image;

FIG. 4E displays a line gap size of 6 µm on the pHEMA hydrogel's microstructure patterned on silicon substrate as a scanning electron microscope image;

FIG. 4F displays a line gap size of 12 µm on the pHEMA hydrogel's microstructure patterned on silicon substrate as a scanning electron microscope image;

DETAILED DESCRIPTION OF AN EXEMPLARY EMBODIMENT

Figure 1B:
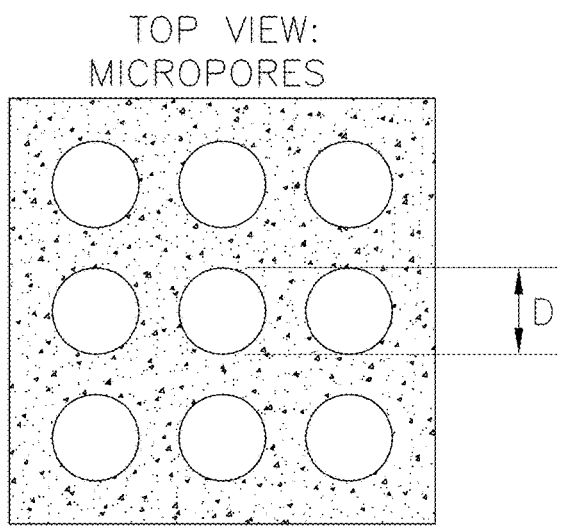
FIG. 1B shows a top view of a schematic of replicated micropores on one-side-textured pHEMA made via the pattern transfer processes of soft lithography.
Figure 1C:
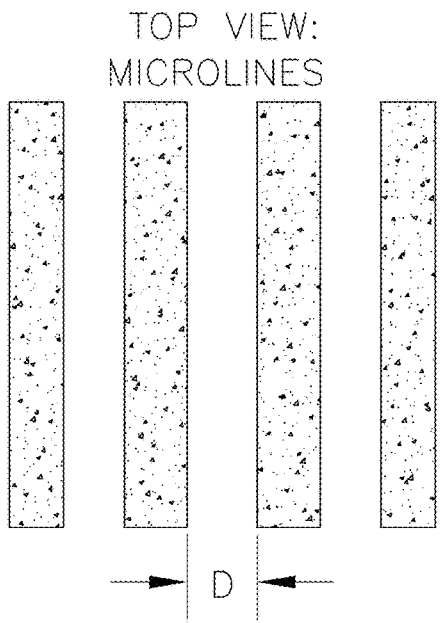
FIG. 1C shows a top view of a schematic of replicated microlines on one-side-textured pHEMA made via the pattern transfer processes of soft lithography.
Figure 1D:
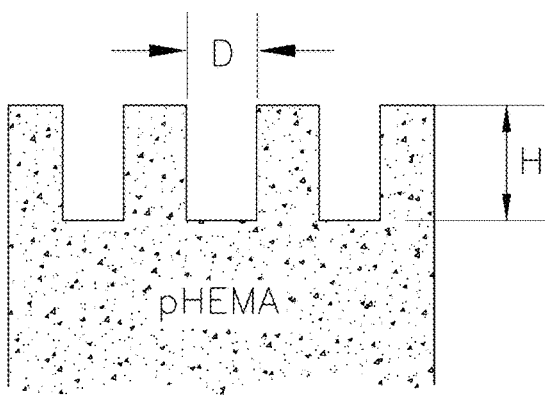
FIG. 1D shows a side view of a schematic of replicated micropores and microlines on one-side-textured pHEMA made via the pattern transfer processes of soft lithography.

To give the pHEMA hydrogel the desired microstructure of the final artificial cornea, templates (e.g., silicon masters) having the desired microstructure (i.e., micropores or microlines) are first fabricated. Referring now to FIG. 1A, a UV light lithography process is used to create a microtextured photoresist layer deposited on the top of silicon by shining UV light through a designed micropatterned photomask. The microtextured photoresist layer is used as etch mask in deep reactive ion etching (DRIE) of a silicon wafer. During the DRIE, the photoresist micropatterns are transferred on to the silicon wafer, where only the silicon wafer area uncovered by the photoresist is etched by the etching gases. Therefore, the photoresist mask layer and the silicon master should share the same dimensions of microtextures. The depth of the silicon microstructure can be controlled by varying the etching time in the process of DRIE. The photoresist residue is then removed from the silicon wafer.

Once the silicon masters are made, the microstructure patterns are transferred to polydimethylsiloxane (PDMS) via a soft lithography technique to form a pair of molds. To this end, uncured PDMS (e.g., in monomer form with a cure agent in a 10:1 ratio) is flow-coated onto the silicon masters. Once fully cured, the PDMS, which now constitutes the molds, is peeled off from the silicon master. (Refer to FIG. 1A)

Figure 2A:
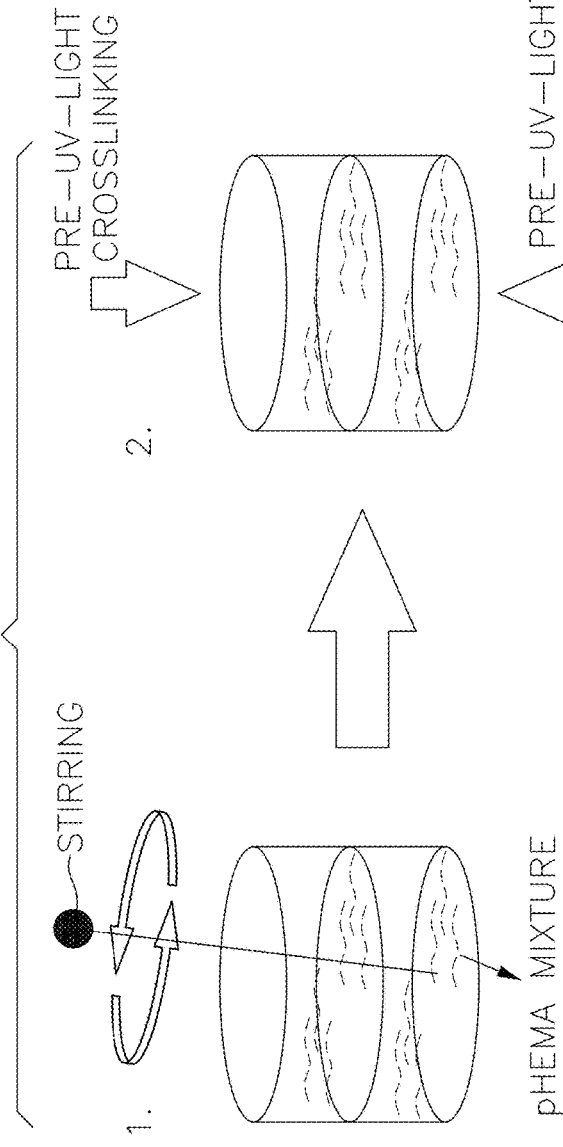
FIG. 2A is a schematic diagram showing the preparation of a viscous pHEMA mixture prior to injection into PDMS molds.
Figure 2B:
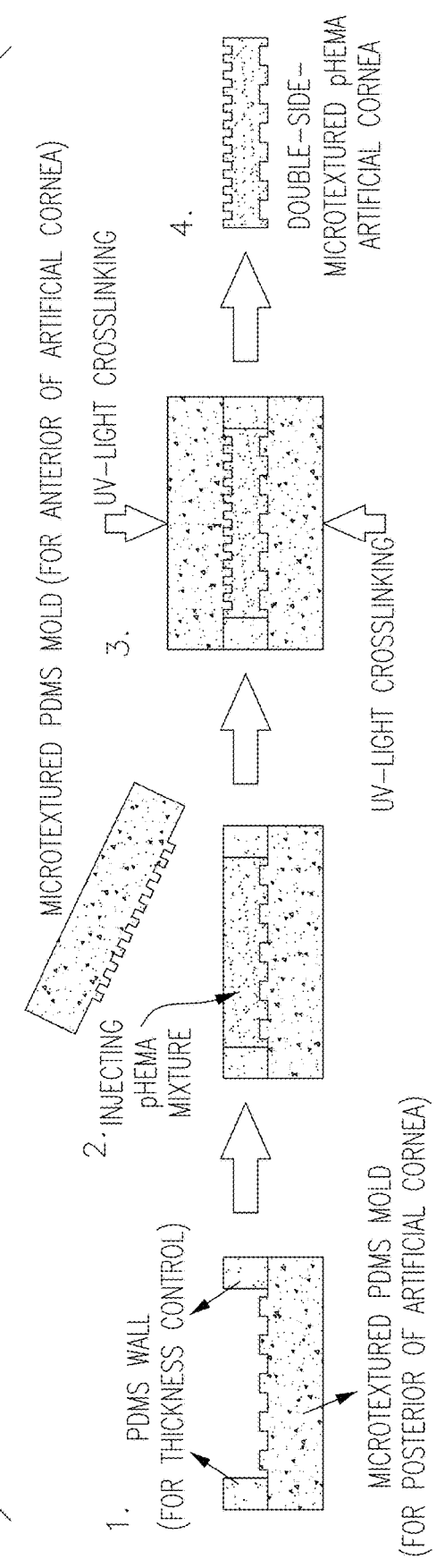
FIG. 2B is a schematic diagram of the use of PDMS molds in the microtexturing process.

Once the molds are prepared, liquid pHEMA monomer (2-Hydroxyethyl methacrylate, Sigma-Aldrich, CAS No.: 868-77-9) is first mixed with an initiator (2-Hydroxy-2-methylpropiophenone 97%, Sigma-Aldrich, CAS No.: 7473-98-5) while being exposed to UV light for a few minutes, resulting in a viscous pHEMA mixture (see FIG. 2A). Additional initiator and crosslinker (Ethylene glycol dimethacrylate, Sigma-Aldrich, CAS No.: 97-90-5) for pHEMA are then added. Once fully mixed and degassed, the pHEMA mixture is slowly poured into a chamber defined by a bottom one of the PDMS molds and non-textured PDMS walls. The other PDMS mold (i.e., the top stamp) is then gently pressed down on top of the pHEMA such that the pHEMA flows into the PDMS microstructures on the top and bottom molds completely, creating an imprint of the PDMS molds' microstructures on the pHEMA material with high fidelity. Thus, the pHEMA microstructures now replicate the microstructures of the silicon masters. The pHEMA and its surrounding structure is then exposed to UV light until the pHEMA is completely cured (see FIG. 2B). The PDMS molds can be peeled off from the cured pHEMA to obtain the desired hydrogel. Then, the pHEMA is quickly washed with ethanol and then with phosphate-buffered saline (approximate pH of 7.4) to remove unreacted chemical residue from the finished pHEMA material's surface.

Figure 3:
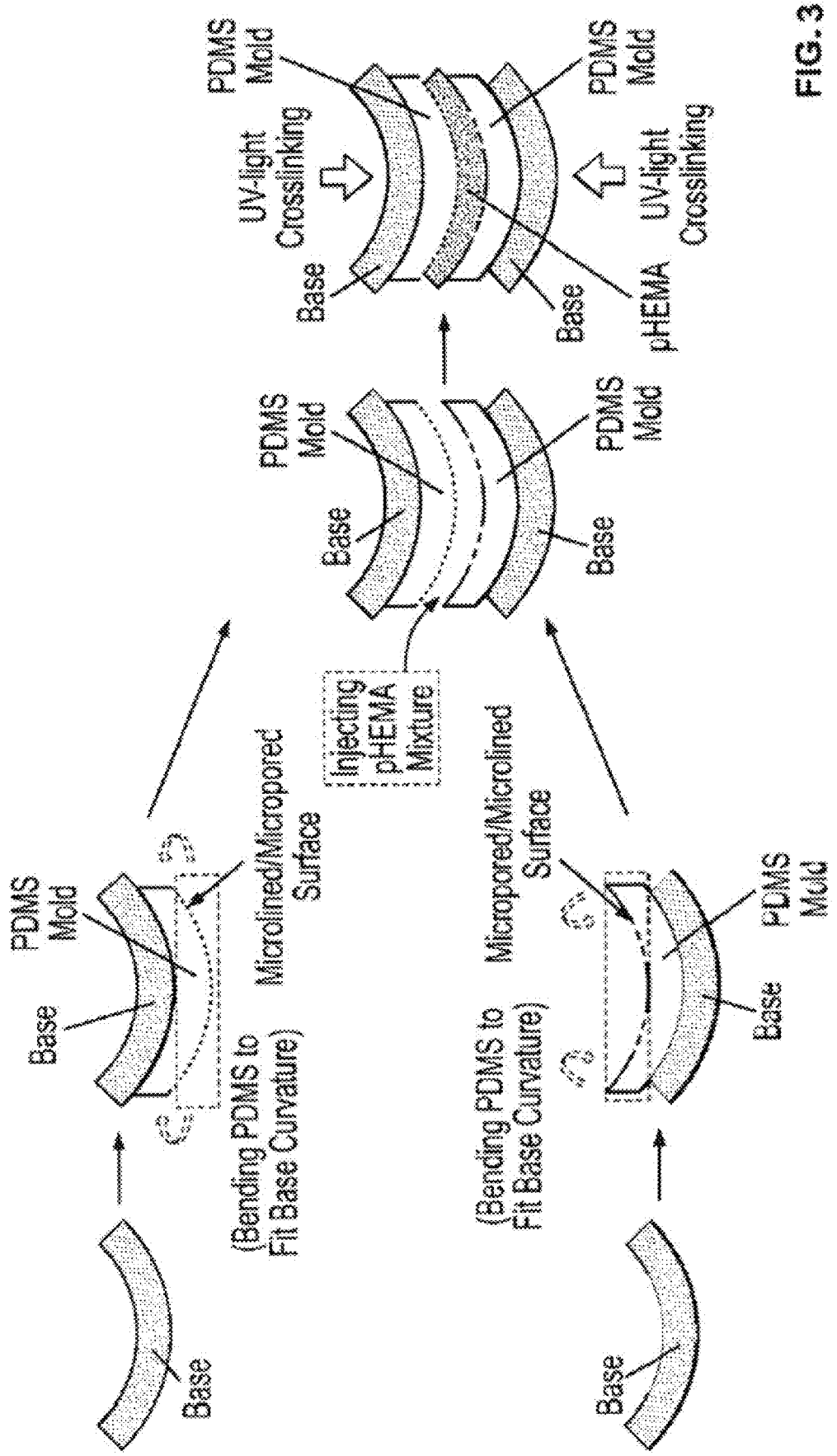
FIG. 3 is a schematic diagram of a molding process to achieve desired curvature of the artificial cornea.

FIG. 3 explains one of the possible methods to achieve the desired curvature on the artificial cornea by using a molding process. The curved base is made of quartz glass (or PDMS). After fixing the bended PDMS mold with microtextures onto two bases by clamps, the uncured pHEMA mixture (after pre-UV-light-crosslinking) can be injected into the gap between two molds for final UV-light crosslinking step.

Referring now to FIG. 4, exemplary microstructures are shown, demonstrating how pore size can be varied. FIGS. 4A, 4B and 4C show micropore diameters of, respectively, 3 μm, 6 μm and 12 μm. FIGS. 4D, 4E and 4F show line gap sizes of, respectively, 3 μm, 6 μm and 12 μm.

Figure 5A:
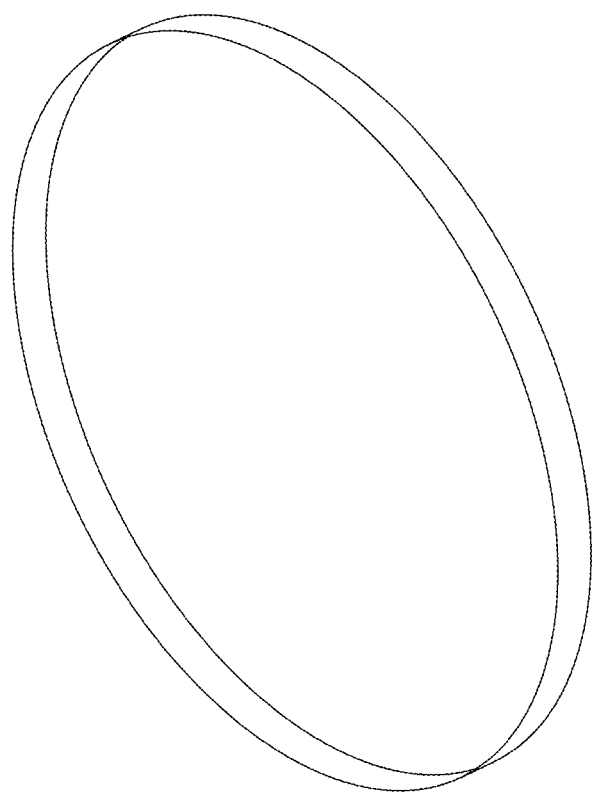
FIG. 5A is a perspective view of an artificial cornea made in accordance with an embodiment of the present invention.
Figure 5B:
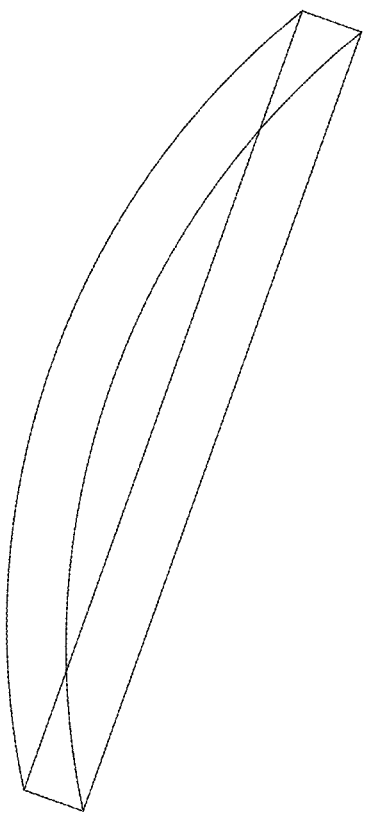
FIG. 5B is a side view of the artificial cornea shown in FIG. 5A.
Figure 5C:
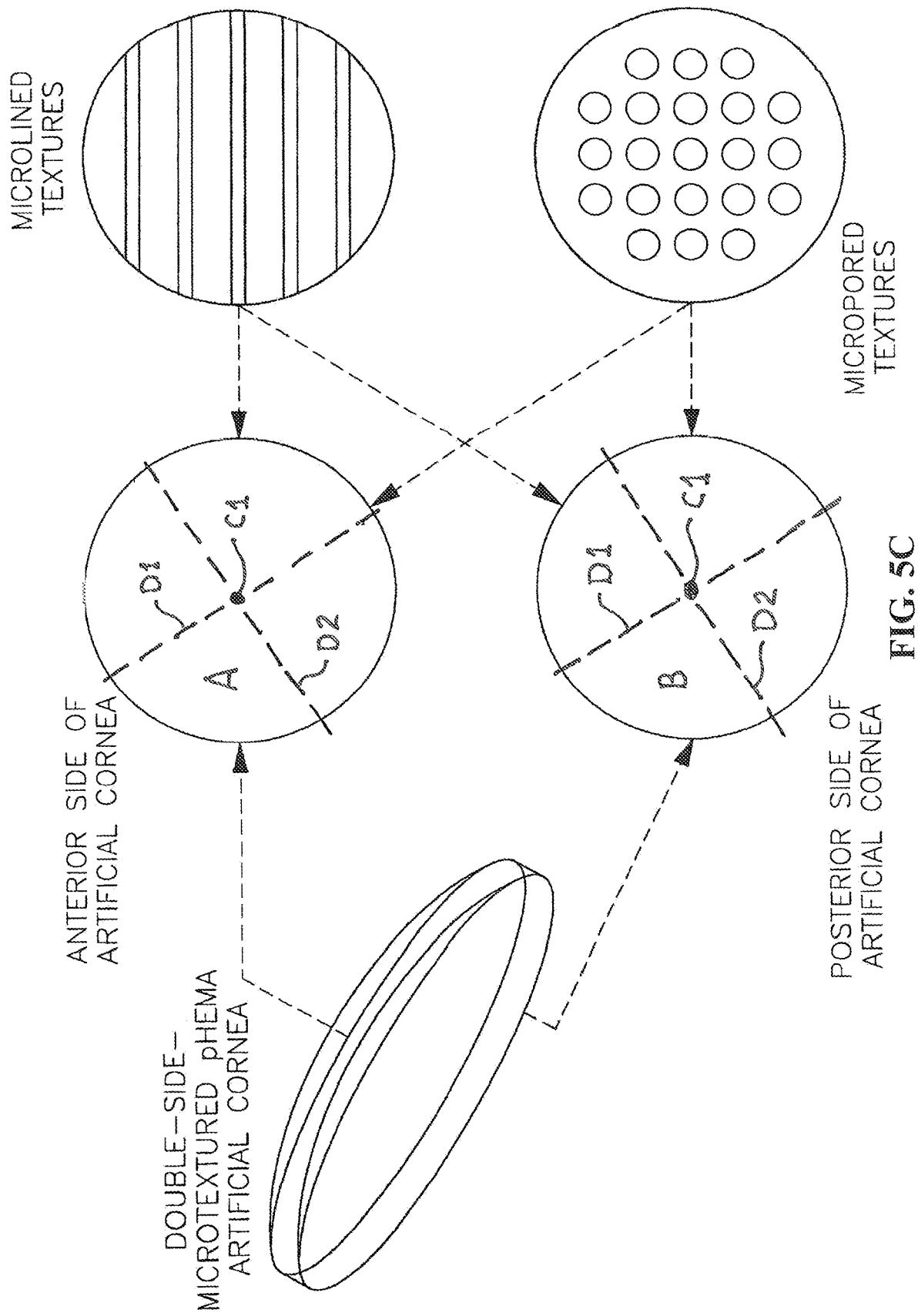
FIG. 5C is a schematic diagram, including an anterior and a posterior view, of an embodiment of the artificial cornea of the present invention having a microline texture on one side and a micropore texture on the opposite side, or the same microline or micropore texture on both sides.

FIG. 5A is a perspective view of an artificial cornea in the form of a disc-shaped body having an anterior side A and a posterior side B, while FIG. 5B is a side view of same. FIG. 5C shows an embodiment of the present invention in which microlines are present on the anterior side A of the artificial cornea, while micropores are present on the posterior face B. The anterior side A has an anterior face extending completely across the implant's disc-shaped body. The posterior side B has a posterior face extending completely across the implant's disc-shaped body. The disc-shaped body also has a first imaginary diameter D1 and a second imaginary diameter D2 extending perpendicular to the first imaginary diameter D1 and intersecting with the first imaginary diameter D1 at an imaginary central axis Cl oriented normal to the anterior and posterior faces of said body and passing through respective central regions thereof. The microlines of the anterior side are distributed throughout the anterior face, including its central region, while the micropores are distributed throughout the posterior face, including its central region.

By way of example, the diameter of the micropores and the width of the microlines' ridges can range from a few micrometers to few tens of micrometers (e.g. larger than 1 μm but less than 100 μm). The depth of the micropores should be smaller than the thickness of the artificial cornea, e.g., less than 2000 μm. The depth of the microlines should be further restricted by their aspect ratios (e.g., maximum ratio of depth to ridge width=3:1) due to the weaker mechanical strength of the pHEMA microlines when the aspect ratios are greater than 3:1. For use with a typical adult, the total thickness of the artificial cornea can lie in a range of from about 500 to about 600 μm, the radius of the artificial cornea can lie in a range of from about 3 to about 5 mm, the radius of its curvature from about 8 mm to about 10 mm, and its Young's Modulus can lie in a range of from about 1 to about 2 MPa. For use with typical infants or individuals with larger corneas (or even larger animals, such as cows), the total thickness of the artificial cornea can lie in a range of from about 100 to about 2000 μm, the radius of the artificial cornea can lie in a range of from about 1 to about 20 mm, the radius of its curvature from about 2 mm to about 30 mm, and its Young's Modulus can lie in a range of from about 0.2 to about 50 MPa.

In manufacturing the artificial cornea, it is desirable to vary its dimensions to suit the recipient. For instance, the thickness of the artificial cornea should be controlled. Another factor to control is the curvature of the artificial cornea so that it suits the patient's eye.

The design of the pHEMA hydrogel is partially motivated by the expectation that the corneal epithelium will be allowed to proliferate well and fast to form a layer of protection and prevent the eyes from bacterial infection, inflammation, stromal melt, or extrusion. The microstructure outer surface of the artificial cornea can be designed to facilitate this outcome. To a similar end, the microstructure of the inner surface of the hydrogel can be designed to allow for fast adhesion of keratocytes (corneal fibroblasts) to the hydrogel, leading to the stable formation of stroma underneath the artificial cornea, thereby decreasing recovery time following the implantation. Enhanced keratocyte adhesion also stabilizes the artificial cornea itself on the top of the eyeball without unnecessary movement, which in conjunction with the softness of the hydrogel makes it ideal for permanent wearing by decreasing discomfort.

Figure 6:
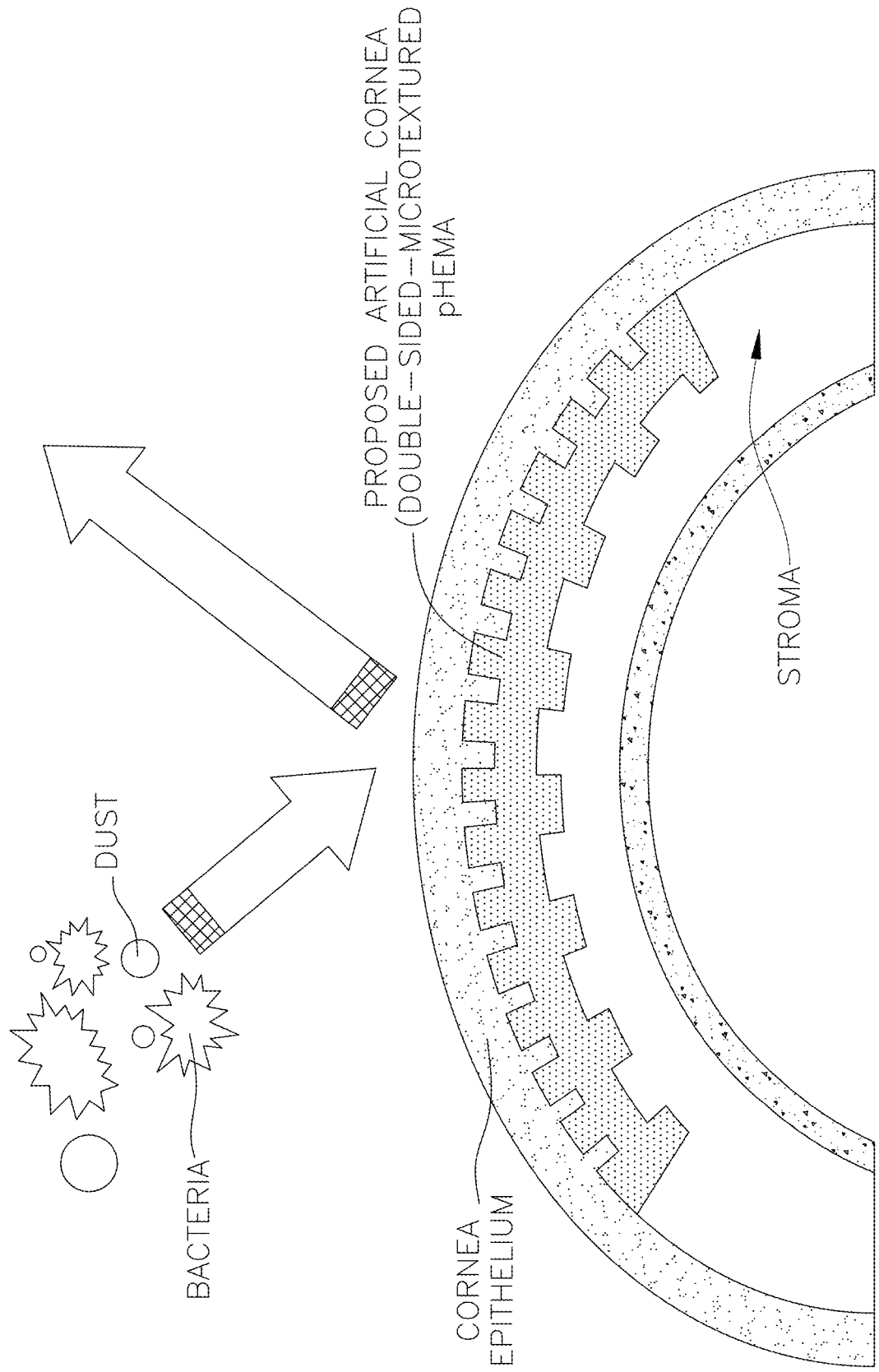
FIG. 6 is a schematic diagram of the implanted double-side-microtextured pHEMA hydrogel functioning as an artificial cornea.

Referring now to FIG. 6, the position of the artificial cornea in the eye can be seen in a situation where the artificial cornea has been inserted into a patient's eye to replace an old malfunctioned cornea. As illustrated in FIG. 6, after the patient's cornea frontier (with dead or damaged tissue) is cut off (to create a pocket to insert an implant) by the surgeons, the artificial cornea of the present invention can be embedded into the cornea stroma pocket to replace the removed tissue. In applying the artificial cornea to the patient's eye, it should be noted that no donor tissue is required for either the manufacture or the implantation of the hydrogel. The pHEMA hydrogel from which the artificial cornea is made is an FDA approved biocompatible material having similar mechanical properties to human tissue. In an embodiment, its water content is larger than 10% by weight.

Further methods are available to improve the physical and chemical properties of the artificial cornea described hereinabove. For example, the incorporation of bioactive molecules (e.g., one or more peptides) can speed up the proliferation of patients' own epithelial cells to cover the whole top surface of the artificial cornea, efficiently, right after surgery, to further prevent potential infection and inflammation. To incorporate peptides into the hydrogel, they can be added into the uncured 2-hydroxyethyl methacrylate solution (i.e., HEMA solution) before final polymerization processes. Alternatively, peptides can be loaded into the pHEMA hydrogel once the gel is polymerized. Peptides with chemotactic and/or chemokinetic can possess the desired biological activity and offer better control of release than such macromolecules. It should be noted that other materials can also be loaded into the micropores, such as tears, to mitigate dryness.

To further improve the lifetime of the artificial cornea described above, co-polymers (e.g., methacrylic acid (MMA)) can also be added into the HEMA solution, during fabrication of the hydrogel, for the polymerization of the pHEMA hydrogel. The weight ratio between the added co-polymer to pHEMA can be any value less than 1:2. Addition of these co-polymers improve the strength and other mechanical properties of the artificial cornea. Another method for improving the lifetime of the artificial cornea implant is altering the concentration of the cross-linker of the pHEMA. The added co-polymer(s) and pHEMA are both FDA approved to be applied to the human body, thus, the biocompatibility of the artificial cornea can be ensured. The Young's Modules of the pHEMA with co-polymer(s) can range from a few megapascals to a few hundred megapascals, which will be larger than the Young's Modulus of the original pHEMA by itself.

An improved pHEMA-based artificial cornea can be made using a method which combines the aforementioned peptides and co-polymers. The resulting product would have sufficient transparency, as aided by the peptides, while also having the improved mechanical properties occasioned by the addition of the co-polymers. Such a product may better resist tear, thereby sparing patients from a subsequent secondary surgery. Therefore, the improved method described above has the potential to fabricate artificial corneas suitable for lifelong use by a patient.

It will be understood that the embodiment described hereinabove is merely exemplary and that a person skilled in the art may make many variations and modifications without departing from the spirit and scope of the present invention.

The invention claimed is:

1. An ocular implant, comprising:
   a disc-shaped body made, at least partially, from a soft pHEMA hydrogel and having an anterior side and a posterior side opposite said anterior side, said anterior side including an anterior face extending completely across said anterior side of said body such that said anterior face has a first central region, and said posterior side including a posterior face extending completely across said posterior side of said body such that said posterior face has a second central region, wherein said disc-shaped body has a first imaginary diameter and a second imaginary diameter extending perpendicular to the first imaginary diameter and intersecting with the first imaginary diameter at an imaginary central axis oriented normal to said anterior and posterior faces of said body and passing through said first and second central regions of said anterior and posterior faces, respectively;
   a first means for integrating said anterior face of said body with a corneal epithelium, said first means comprising a first plurality of micropores having diameters of larger than 1 micron to less than 100 microns, said first plurality of micropores being formed in and distributed throughout said anterior face of said body, including said first central region, and said first plurality of micropores being adapted to promote epithelial cell growth and adhesion on said anterior face of said body; and
   a second means for integrating said posterior face of said body with a stroma, said second means comprising a second plurality of micropores with diameters of larger than 1 micron to less than 100 microns, said second plurality of micropores being formed in and distributed throughout said posterior face of said body, including said second central region, and said second plurality of micropores being adapted to promote growth and adhesion of keratocytes to said posterior face of said body.

2. The ocular implant of claim 1, wherein said body includes one or more co-polymers incorporated into said hydrogel, said one or more co-polymers comprising methacrylic acid.

3. The ocular implant of claim 1, wherein said body includes one or more bioactive molecules incorporated into said hydrogel, said one or more bioactive molecules comprising one or more peptides.

4. The ocular implant of claim 1, wherein said body has a thickness in a range of from about 100 microns to about 2000 microns.

5. A method of repairing a damaged cornea, comprising the steps of:
   providing an ocular implant which comprises a disc-shaped body made, at least partially, from a soft pHEMA hydrogel and having an anterior side and a posterior side opposite said anterior side, said anterior side including an anterior face extending completely across said anterior side of said body such that said anterior face has a first central region, and said posterior side including a posterior face extending completely across said posterior side of said body such that said posterior face has a second central region, wherein said disc-shaped body has a first imaginary diameter and a second imaginary diameter extending perpendicular to the first imaginary diameter and intersecting with the first imaginary diameter at an imaginary central axis oriented normal to said anterior and posterior faces of said body and passing through said first and second central regions of said anterior and posterior faces, respectively, a first means comprising a plurality of micropores having diameters of larger than 1 micron to less than 100 microns, said first plurality of micropores being formed in and distributed throughout said anterior face of said body, including said first central region, and a second means comprising a plurality of micropores having diameters of larger than 1 micron to less than 100 microns, said second plurality of micropores being formed in and distributed throughout said posterior face of said body, including said second central region;
   lesioning the damaged cornea of a patient;
   removing dead or damaged tissue from said damaged cornea to surgically create a cornea stroma pocket;
   embedding said ocular implant into said cornea stroma pocket such that said posterior face on said posterior side of said body, and hence said second plurality of micropores, interface with said stroma pocket; and
   allowing said ocular implant to remain in said cornea stroma pocket such that said first means promotes epithelial cell proliferation and adhesion on said anterior face of said body, thereby inhibiting extrusion of said ocular implant, and such that said second means adheres and grows keratocytes to said posterior face of said body, thereby leading to the stable formation of stroma underneath said ocular implant.

6. The ocular implant of claim 1, wherein each micropore of said first plurality of micropores does not extend to said posterior face of said body and wherein each micropore of said second plurality of micropores does not extend to said anterior face of said body.

7. The method of claim 5, wherein said ocular implant has a Young's modulus that ranges from 0.2 MPa to 50 MPa.

8. The ocular implant of claim 1, wherein said ocular implant has a Young's modulus that ranges from 0.2 MPa to 50 MPa.

9. The method of claim 5, further comprising the step of incorporating one or more co-polymers into said hydrogel of said body, thereby improving the mechanical strength of said ocular implant.

10. The method of claim 5, further comprising the step of incorporating one or more bioactive molecules into said hydrogel of said body, thereby improving proliferation of epithelial cells on said anterior face of said body.

11. The method of claim 5, wherein said ocular implant is adapted to be integrated with the stroma of a patient's eye.

12. The ocular implant of claim 6, wherein each micropore of said first and second plurality of micropores has a depth which is less than 2000 microns.

13. The method of claim 5, wherein said body has a thickness in a range of from about 100 microns to about 2000 microns.

14. The method of claim 5, wherein each micropore of said first and second plurality of micropores has a depth which is less than 2000 microns.

* * * * *